United States Patent [19]

Whiteside

[11] Patent Number: 4,474,177

[45] Date of Patent: Oct. 2, 1984

[54] METHOD AND APPARATUS FOR SHAPING A DISTAL FEMORAL SURFACE

[75] Inventor: Leo A. Whiteside, Chesterfield, Mo.

[73] Assignee: Wright Manufacturing Company, Arlington, Tenn.

[21] Appl. No.: 473,465

[22] Filed: Mar. 9, 1983

[51] Int. Cl.³ .................................................. A61F 5/04
[52] U.S. Cl. .............................. 128/303 R; 128/92 R; 128/92 E
[58] Field of Search ............. 128/92 H, 92 C, 92 CA, 128/92 BC, 92 EA, 92 EB, 92 E, 303 R

[56] References Cited

U.S. PATENT DOCUMENTS 4,211,228  7/1980  Cloutier ........................... 128/92 E
4,306,550 12/1981  Forte et al. ...................... 128/92 E
4,421,112 12/1983  Mains et al. ...................... 128/92 E

OTHER PUBLICATIONS

Dow Corning Wright, "Whiteside Ortholoc TM Total Knee System", 1983, (instant invention).
T.A.R.A. TM Articular Replacement System for Hemi and Total Hip Arthroplasty, 6 pages, Form No. 779-29, Issue Date: 0601-44, DePuy Division of Boehringer Mannheim Corp., Warsaw, Ind. 46580.
The Modified Austin Moore Design with Porocoat TM, Surgical Procedure, 4 pages, Form No. 281-9, issue date 2/81, DePuy Division, Warsaw, Ind. 46580.
"The Howmedica ® Universal TM Total Knee Instrumentation System", Brochure No. H-2026-1, 1/82, 15MB, (1980), Howmedica Inc., Rutherford, NJ 07070.
"New Jersey Tricompartmental Total Knee Replacement Surgical Procedure by Frederick F. Buechel, M.D.", 13 pages, Issue Date 1/81, Form No. 1280-32, DePuy Div., Boehringer Mannheim Corporation, Warsaw, Indiana 46580.
Richards, "RMC TM Total Knee System" 1978, Rev. 9/79, 3246.
Zimmer, "Cloutier TM II Non-Constrained Total Knee System", 1981, 81-038-5701-0968/SMZ.
Dow Corning Wright, "Lacey Condylar Total Knee System", 1983, L095-0104.
Zimmer, "Sheehan Knee Prosthesis", 1981, 81-038-84-54-0906/ZMZ.

Primary Examiner—C. Fred Rosenbaum
Assistant Examiner—C. W. Shedd
Attorney, Agent, or Firm—Richard E. Rakoczy

[57] ABSTRACT

The present invention provides a method and apparatus for preparing the distal surface of a femur to receive a distal femoral prosthesis employing an intramedullary reamer which is used to internally locate the central long axis of the femur, an intramedullary alignment guide which is inserted into the space left in the intramedullary canal upon removal of the reamer and at least one femoral surface modifying instrument which cooperatively engages with a guide handle attached to the intramedullary alignment guide to accomplish the shaping of the distal femoral surface. The intramedullary alignment guide has a rod portion extending into the femoral intramedullary canal whose central long axis corresponds with the central long axis of the femur. The guide handle is attached to that rod portion at a preselected angle such that the shaping instruments fixed thereto assume the proper alignment with respect to the central long axis of the femur such that the distal femoral surface is shaped relative to that axis in a simple and accurate manner.

10 Claims, 23 Drawing Figures

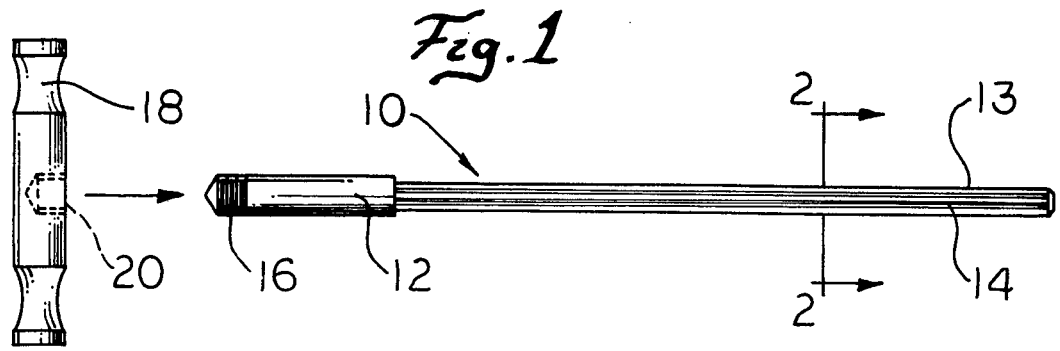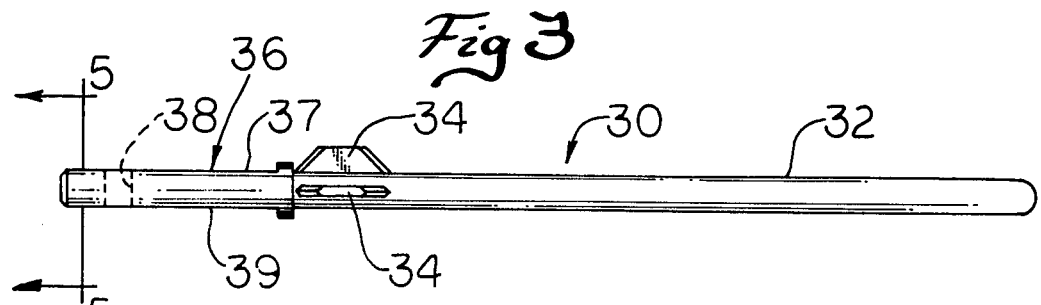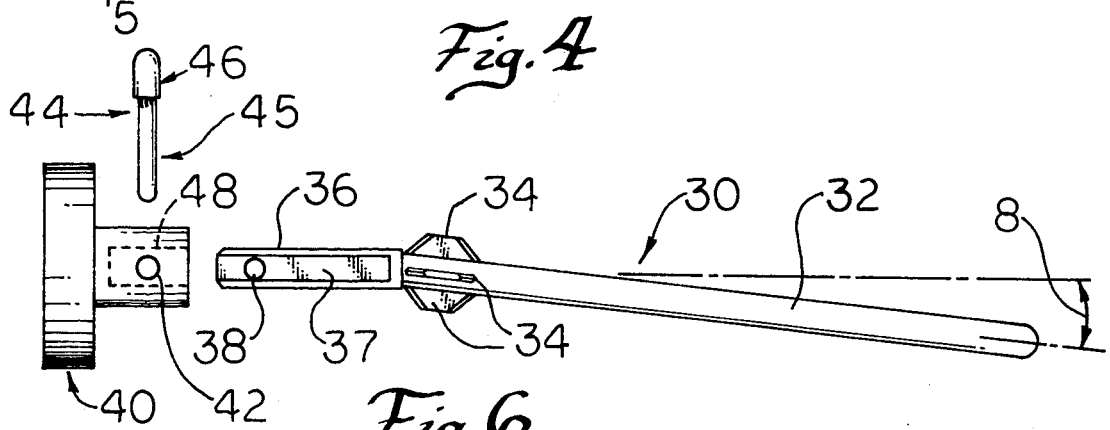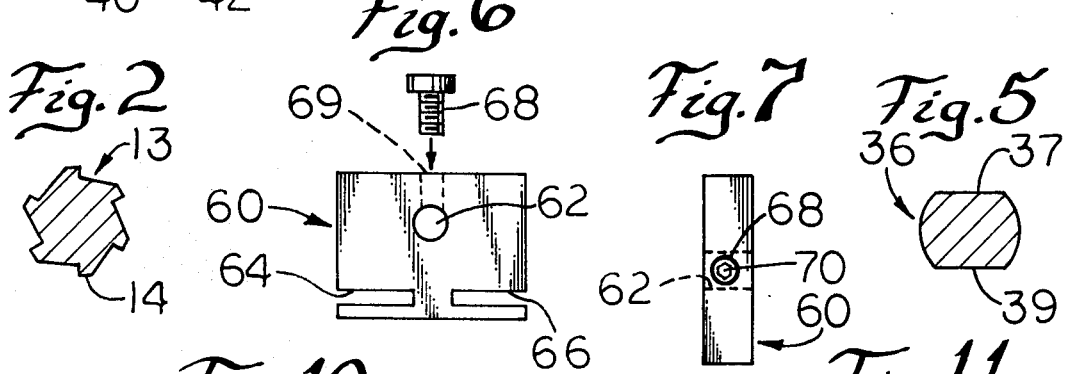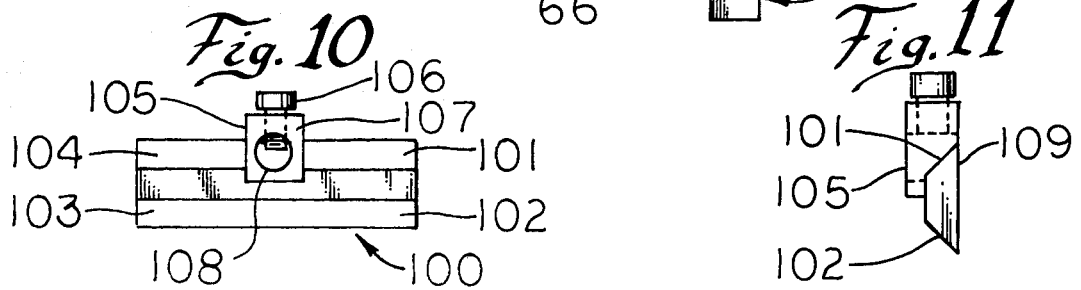

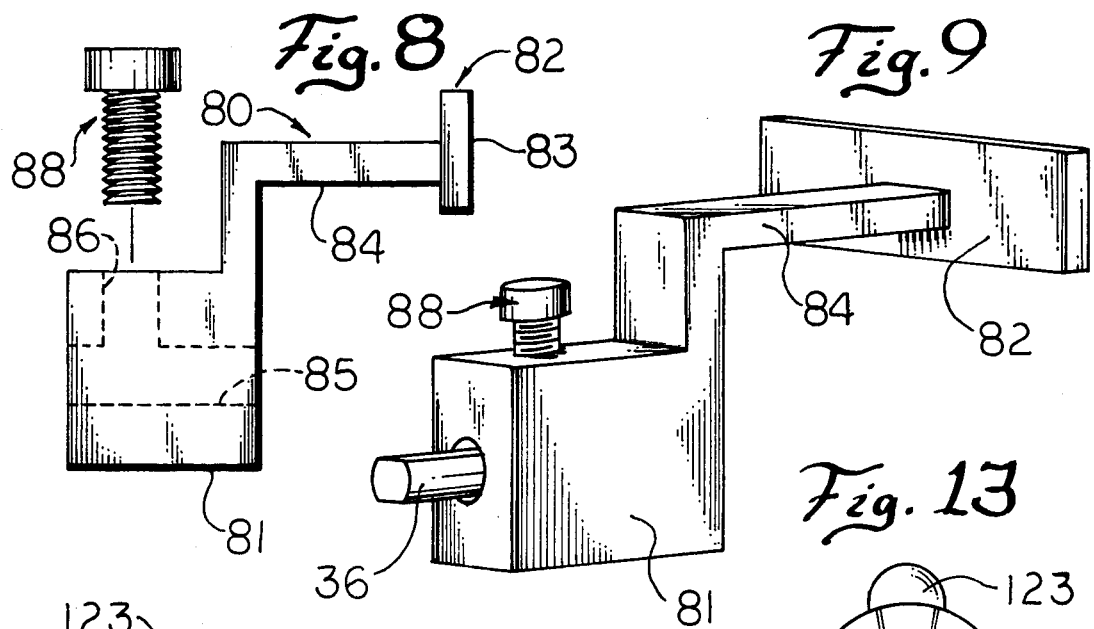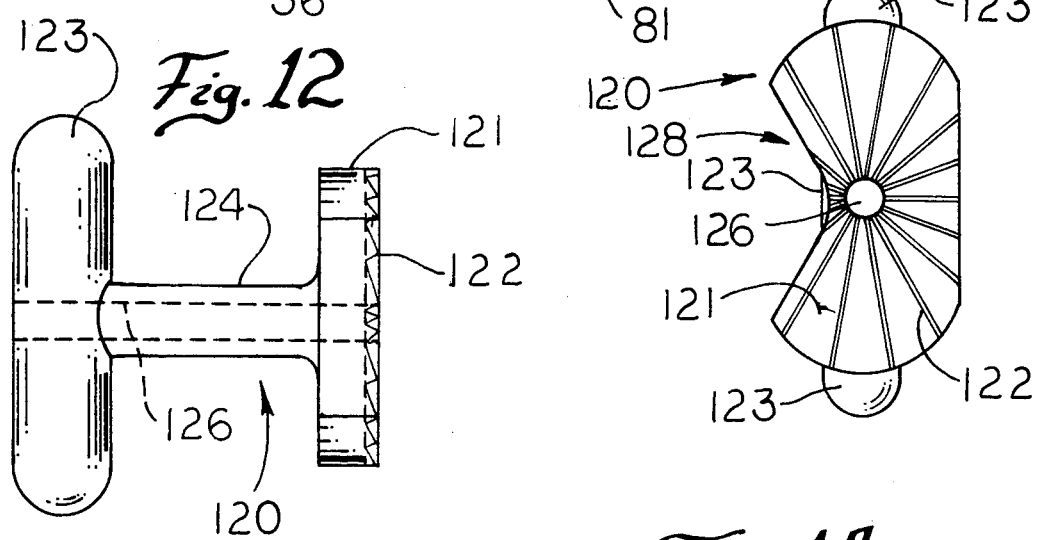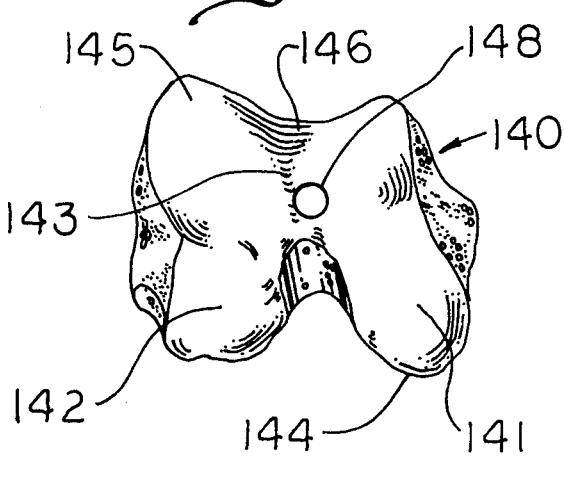

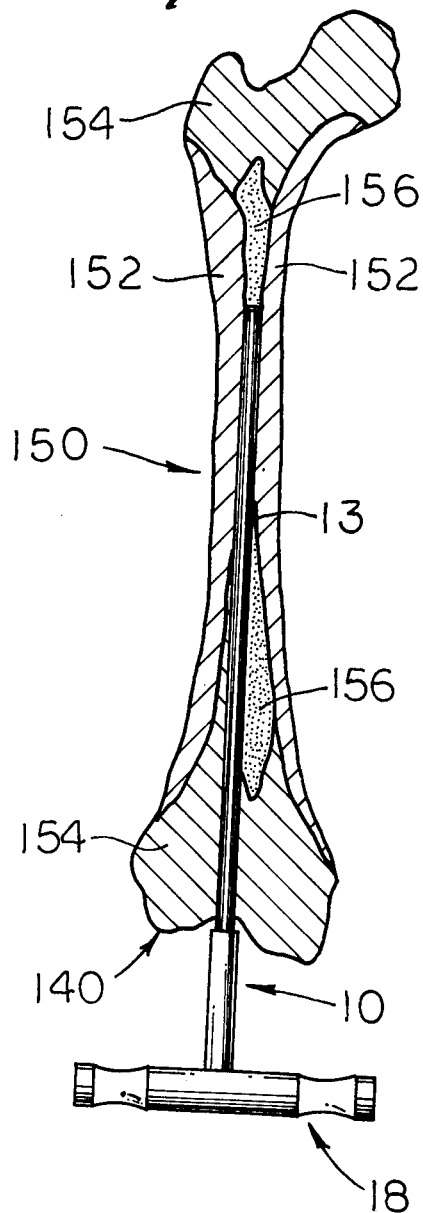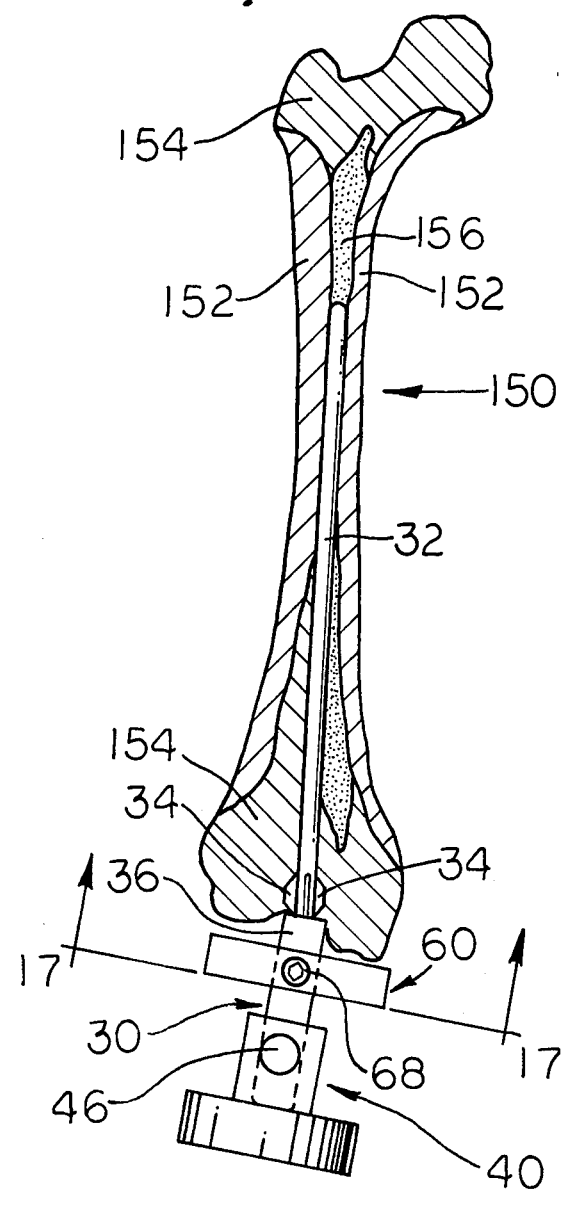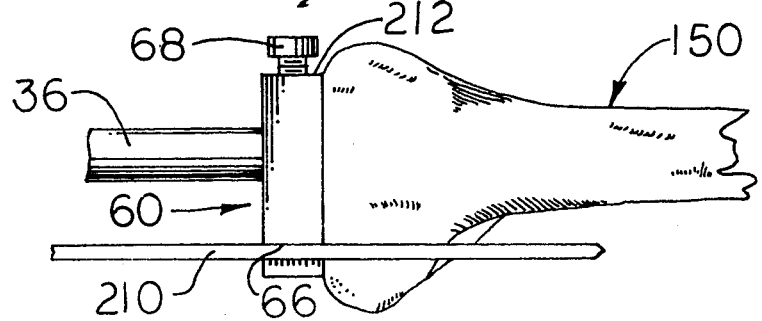

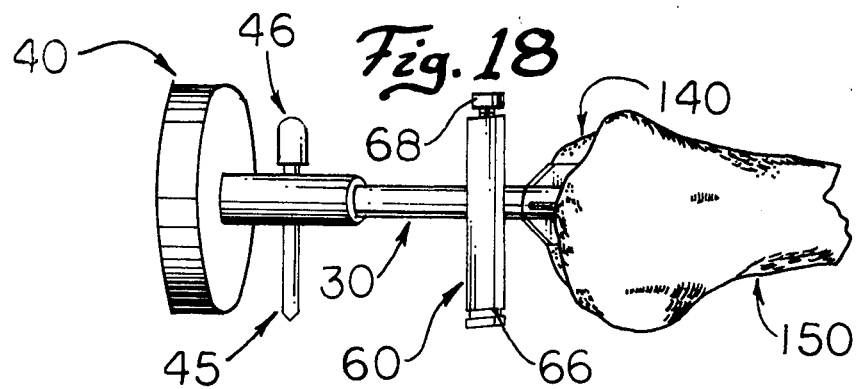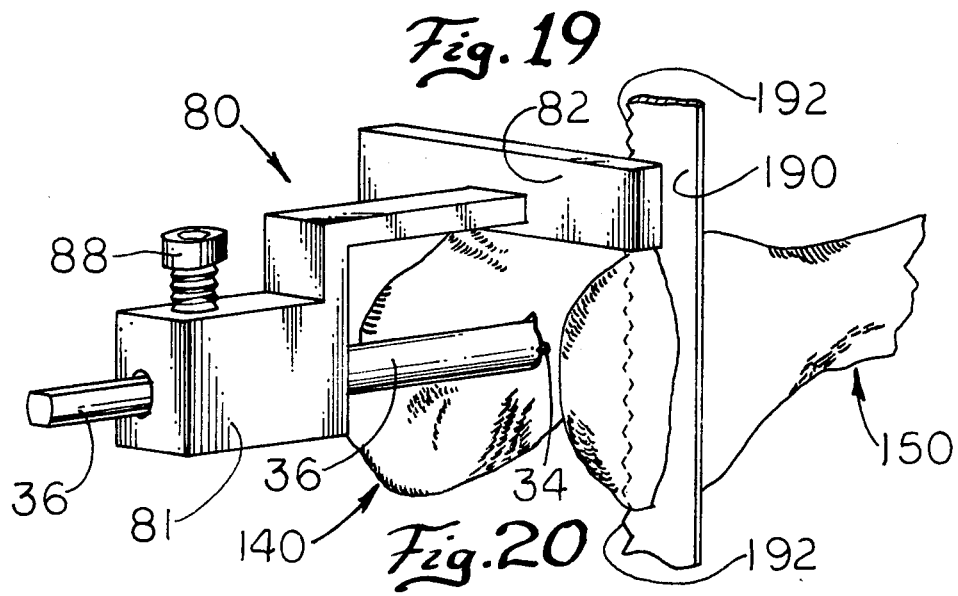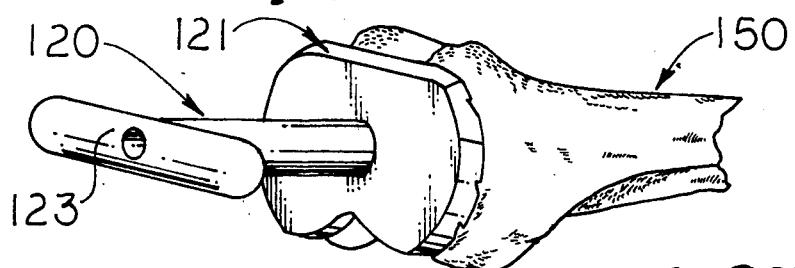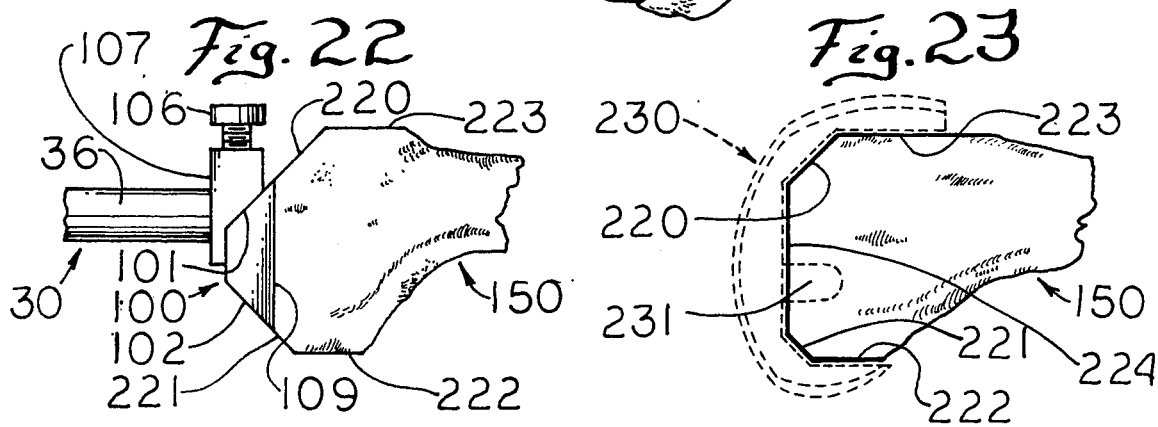

METHOD AND APPARATUS FOR SHAPING A DISTAL FEMORAL SURFACE

BACKGROUND OF THE INVENTION

This invention relates to a method of shaping the distal surface of a human femur using certain alignment guides and instruments to prepare that surface to receive a distal femoral prosthesis and also relates to certain apparatus used in that method.

Various types of instruments and methods have been developed to enable a surgeon to affix a distal femoral knee prosthesis to the human femur. Since the purpose for affixing such a prosthesis is to restore the patient's ability to walk after disease or other traumatic causes have impaired that ability, it is important that the prosthesis be attached to the femur in such a manner that it will approximate as closely as possible the natural condyles which the prosthesis is replacing. If the prosthesis is not properly affixed with respect to the femur, an unnatural gait or other complications can result.

It is a common practice to use the long central axis of the femur as a guide in determining the manner in which the distal femoral surfaces should be shaped to receive a properly aligned distal femoral prosthesis. Generally a pre-operative single, long anterior-posterior radiograph showing the shaft of the tibia and femur is made and the angle of the central long axis of the femur relative to the vertical axis of the body (physiological valgus, generally from 5°-12°) is visualized. That angle is then used as a reference when the distal femoral surface is shaped using various cutting instruments and guides. In one such method, a long axial alignment jig (rod) is employed which is positioned over the outside surface of the patient's leg in a position which the surgeon visually determines to correspond to the central long axis of the femur and the femur is shaped relative to the alignment of that rod. One example of the manner in which the distal femoral surface is shaped to receive a prosthesis using an external alignment rod is shown in "The HOWMEDICA ® Universal ™ Total Knee Instrument System", brochure no. H-2026-1 1/82 15M B (1980) from Howmedica, Inc., Orthopaedics Division, Rutherford, NJ 07070 which is hereby incorporated by reference.

The external alignment rod has a disadvantage in that the surgeon is relying upon visual and tactile means for positioning in alignment rod since the patient's skin covers the major portion of the femur and screens it from view. Finding the central long axis of the femur of the obese person can present further difficulties.

The use of a relatively short femoral alignment rod in a method for shaping the distal femoral surface is shown in a brochure entitled "New Jersey Tricompartmental Total Knee Replacement Surgical Procedure by Frederick F. Buechel, M.D", 13 pages, issue date 1/1981, Form No. 1280-32, from DePuy Division, Boehringer Mannheim Corporation, Warsaw, Ind. 46580. Part of this procedure employs a femoral alignment rod to hold a femoral resection guide against the distal femoral surface after a drill bit is used to create a shaft for the femoral alignment rod. The shaft is drilled in such a manner that the drill bit and, later, the alignment rod rests inside the intramedullary canal against the posterior femoral cortex. After the anterior and posterior femoral articular surfaces are cut, the alignment pin and the femoral resection guide positioner are removed and an extension-tension femoral alignment guide employing an external alignment rod is employed to resect the inferior femoral articular surface to the desired degree of physiological valgus (5°-12°). That guide is removed and an oblique osteotomy guide, a portion of which is designed to fit into the shaft for the femoral alignment rod, is then employed to resect and drill prosthesis mounting holes in the distal femoral surface. The final femoral resection is accomplished with a recessing guide which fits over the oblique osteotomy guide.

In both of the above procedures, the alignment rods employed do not enable a surgeon to accurately follow the central long axis of the femur because the femur is not exposed to visual observation along its length. This can especially become a problem when the femur possesses a deformity which may somewhat alter its true central axis.

SUMMARY OF THE INVENTION

There appears to be a need for a method of shaping the distal surface of a femur to receive a distal femoral prosthesis which enables a surgeon to shape that surface as accurately as possible while using the true central long axis of the femur as a guide.

One object of the present invention is to provide a means by which the central long axis of the femur can be more accurately determined through the use of an instrument passing through the intramedullary canal of the femur.

It is another object of the present invention to provide an alignment guide upon which all femoral surface shaping instruments can be mounted such that the alignment of each instrument is always made relative to the central long axis of the femur.

It is another object of the present invention to provide a method for overcoming the detrimental effects which deformities in the femur cause in locating the central long axis and enabling a surgeon to more accurately shape a distal femoral surface of such a femur to receive a distal femoral prosthesis.

It is a further object of the present invention to provide a plateau planer to provide the distal femoral surface with a much smoother and planar surface than is typically obtained with an oscillating saw. Shaping instruments can be rested against that accurately planed, level surface to provide more accurate shaping of the other distal femoral surfaces. That accurately planed, level distal femoral surface is highly desirable when a distal femoral prosthesis employing a cementless fixation means such as a porous bone ingrowth coating is to be affixed to the femur.

These and other objects of the present invention are provided by a method which comprises boring an entry point for an intramedullary reamer through the distal femoral surface at a point approximating the central long axis of the femur; advancing the intramedullary reamer through the entry point and on up through the intramedullary canal while allowing the reamer to follow and stay within the intramedullary canal until the reamer reaches the narrowest point of the intramedullary canal; removing the reamer and substituting for it an intramedullary alignment guide having a guide handle set at a preselected angle relative to the central long axis of the femur; attaching at least one distal femoral surface modifying instrument to the handle to enable the distal femoral surface to be shaped relative to the central long axis of the femur; shaping the surface and repeatedly adding other instruments to the handle and modifying the surface until the appropriately shaped distal femoral surface is obtained, removing the intramedullary alignment rod and trimming any remaining bone from the distal femoral surface.

This invention also relates to an intramedullary alignment guide in combination with at least one distal femoral surface modifying instrument which cooperatively engages with the intramedullary alignment guide and enables the distal femoral surface to be shaped relative to the central long axis of the femur.

BRIEF DESCRIPTION OF THE DRAWINGS

The above and other objects, features and advantages of the present invention will become apparent to those skilled in the art upon an examination of the following description and drawings which are merely illustrative of the present invention.

In the Drawings:

FIG. 1 is an exploded plan view of an intramedullary reamer and its handle.

FIG. 2 is a cross-section taken along section line 2—2 of FIG. 1.

FIG. 3 is a view of an intramedullary alignment guide taken from the side.

FIG. 4 is a plan view of the guide of FIG. 4, an impactor 40 and locking pin 44.

FIG. 5 is a cross-section taken long section line 5—5 of FIG. 4.

FIG. 6 is an exploded view of an anterior-posterior femoral shaping instrument and its locking bolt 68 taken from the front.

FIG. 7 is a plan view of FIG. 6 showing locking bolt 68 in place.

FIG. 8 is a view of a distal femoral shaping instrument and its locking bolt 88 taken from the side.

FIG. 9 is a perspective view taken from the rear and slightly to the side of FIG. 8 with locking bolt 88 and intramedullary alignment guide handle 36 in place.

FIG. 10 is a view of a bevel shaping instrument taken from the front.

FIG. 11 is a side view of FIG. 10.

FIG. 12 is a side view of a plateau planer instrument.

FIG. 13 is a view of the instrument of FIG. 12 taken from below.

FIG. 14 is a perspective view of a distal femoral surface showing entry point 148 for the reamer.

FIG. 15 is a cross-sectional view of a femur showing the intramedullary reamer of FIG. 1 in place.

FIG. 16 is a cross-sectional view of a femur showing the intramedullary alignment guide of FIG. 3 in place.

FIG. 17 is a view taken along section line 17—17 of FIG. 16 showing proper alignment of the guide relative to the femur.

FIG. 18 is a perspective view taken from the side of FIG. 16 showing the alignment of guide 30.

FIG. 19 is a perspective view taken from the rear and slightly to the side showing the distal femoral shaping instrument in place.

FIG. 20 is a perspective view of a plateau planer instrument in place.

FIG. 21 is a side perspective view of an anterior-posterior femoral shaping instrument in place.

FIG. 22 is a side perspective view of a bevel shaping instrument in place.

FIG. 23 is a side perspective view of an appropriately shaped distal femoral surface showing the outline of a distal femoral prosthesis affixed thereto.

DETAILED DESCRIPTION OF THE INVENTION

Referring to the Drawings, FIG. 1 depicts a preferred form of an intramedullary reamer 10 which is a rod having a portion 13 which is intended to enter the intramedually canal of the femur and has a plurality of cutting ridges 14 situated about its circumference. Portion 13 has an outer diameter (including the cutting ridges) of such a dimension that it approximates the narrowest portion of the intramedullary canal of the femur. FIG. 2 shows the portion 13 and the cutting ridges 14 in cross-section. In the preferred embodiment shown, six cutting ridges are equidistantly situated about the circumference of portion 13. The remaining portion of reamer 10 is preferably a smooth portion 12 of a slightly larger diameter than portion 13 which is intended to contact the distal femoral surface and thereby indicate when the reamer is fully inserted within the intramedullary canal as will be described infra. The end of portion 12 contains threads 16 or some other means by which opening 20 of handle 18 may be fitted over and secured to the end of portion 12 to enable a twisting motion to be imparted to reamer 10 during use. In a preferred embodiment, portion 13 is 10" (254 mm) in length and 0.359" (9.12 mm) in outer diameter from the top of one raised ridge to the ridge opposite it) and portion 12 is about 3.6" (91 mm) in length and 0.495" (12.6 mm) in outer diameter where the symbol" means inches and the symbol mm means millimeters. For use with a femur having a significant degree of deformity, a reamer wherein portion 13 is 7" (178 mm) can be used.

FIG. 3 shows intramedullary alignment guide 30 from the side showing rod portion 32 which is adapted to fit within the space left in the femur by the reamer 10 (preferably portion 32 is 10" (245 mm) in length and 0.375" (9.53 mm) in outer diameter when the aforementioned preferred 10" reamer is employed). In this embodiment, locking fins 34 are employed as a means to fix rod portion 32 within the femur prior to beginning the shaping of the femur. Guide handle 36 contains flattened regions 37 and 39 and hole 38 passing through handle 36.

As can be better seen in FIG. 4, the long central axis of guide handle 36 is attached to and set at an angle shown at reference numeral 8 away from the long central axis of rod portion 32, generally preferred values for angle 8 are 3°, 5°, 7° and 9° although others may be required for particular patients. It is also possible, but much less desirable, to employ an intramedullary alignment guide wherein the angle 8 is zero degrees because all of the hereinafter described surface modifying instruments would have to be suitably configured to shape the femur to the correct angle and a separate set of instruments would be needed for each angle required. Guide 30 contains three locking fins 34. With the exception of the locking fins 34, guide 30 is symmetrical and when flattened surface 37 is superior, the guide 30 can be used for shaping a left femur. When flattened surface 39 is superior, guide 30 can be used for shaping the right femur.

FIG. 4 also depicts intramedullary alignment guide impactor 40 and locking pin 44 having locking pin portion 45 which is slightly smaller in diameter than hole 42 which passes through both sides of impactor 40. Impactor 40 is attached to guide 30 by inserting handle 36 into inset 48, aligning holes 38 and 42 and inserting portion 45 through both holes until handle 46 which is slightly larger in diameter than hole 42 contacts impactor 40.

FIG. 5 more clearly shows the flattened portions 37 and 39 of handle 36. As will become evident, flattened portions 37 or 39 cooperatively engage with locking bolts found on the hereinafter-described shaping instruments to cause them to properly align with the guide handle.

For the purposes of the present invention, the term "femoral surface modifying instrument" shall include instruments serving as cutting (resection) or shaping guides which do not directly act to shape the femoral surfaces as well as instruments such as planers which directly act to modify the surface of the femur.

FIG. 6 shows a femoral surface modifying instrument in the nature of an anterior-posterior cutting guide 60 having passage 62 (0.500" (12.7 mm) outer diameter when preferred guide handle 36 of 0.495" (12.6 mm) outer diameter is employed) adapted to cooperatively engage handle 36 of guide 30. The upper portion of slots 64 and 66 are employed as a saw guide to resect the posterior portion of the distal femoral lateral and medial condyles while the top portion of cutting guide 60 situated on either side of locking bolt 68 (which is inserted into threaded hole 69) are used as a saw guide for cutting the anterior distal femoral condyles. The size of the cutting guide 60 and the distance between the slots 64 and 66 and the upper surfaces of cutting guide 60 relative to the passage 62 are selected to conform to the shape of the distal femoral surface required to fit a preselected distal femoral prosthesis.

It should also be evident that for this and the hereinafter-described femoral surface modifying instruments, all resections and modifications of the femur are made relative to the position of, in this case, passage 62 and thus, relative to the long central axis of the femur which passes through the center of handle 36 and passage 62.

FIG. 7 shows the top surface of guide 60 with hole 62 shown in outline form and with locking bolt 68 with a hex-head inset 70 shown in position.

FIG. 8 is a side preferred view of a femoral surface modifying instrument in the nature of a distal femoral condyle cutting guide 80 having a guideplate 82 having a cutting guide surface 83 held transverse to the central long axis of handle 36 and attached to main body 81 by means of arm 84. Main body 81 contains central passage 85 adapted to cooperatively receive the guide handle 36 (not shown) of intramedullary alignment guide 30 and threaded passage 86 adapted to receive locking bolt 88 to fixedly secure guide handle 36 to the main body 81 in proper alignment with guide 30.

FIG. 9 shows cutting guide 80 of FIG. 8 with guide handle 36 in place and with locking bolt 88 in position to secure main body 81 to guide handle 36. Cutting guide 80 is likewise designed to modify the distal femoral condyles to suit a preselected distal femoral prosthesis.

FIG. 10 shows a distal femoral surface modifying instrument in the nature of a bevel cutting guide 100 having anterior medial and lateral femoral condyle resection guideplates 101 and 104 and posterior medial and lateral femoral condyle resection guideplates 102 and 103. In FIG. 10, guideplates 101, 102, 103 and 104 are situated at a 45° angle with respect to surface 109, but other angles may be appropriate since the angles selected will be dependent upon the configuration of the distal femoral knee prosthesis for which the femur is being shaped to receive. Main body 105 holds the guideplates in a fixed relationship with respect to guide handle 36 (not shown) by means of passage 108 which cooperatively engages guide handle 36 as it passes through main body 105. Guide handle 36 is secured to main body 105 in proper alignment with respect to the central long axis of the handle 36 and thereby with respect to the central long axis of the femur by means of locking bolt 106 passing through threaded passage 107.

FIG. 11 is a side view of cutting guide 100 showing the relationship of resection guideplates 101 and 102 to main body 105 and further showing the planar back surface 109 of cutting guide 100.

FIG. 12 shows a distal femoral surface modifying instrument in the nature of a plateau planer 120 having a planar abrading surface 121 which, in the preferred embodiment shown, possesses a series of equally spaced cutting ridges 122 which are planar and are situated transverse to the central long axis of guide handle 36 (not shown). That guide handle is inserted through passage 126 and thereby enables the plateau planer 120 to be freely rotated against the distal femoral surface (not shown) about the central long axis of the guide handle 36 and thus rotated about the central long axis of the femur. Planar abrading surface 121 is rotated about the distal femoral surface by imparting a twisting motion to handle 123 which is attached to abrading surface 121 by means of shaft 124.

FIG. 13 shows plateau planer 120 from below and more clearly shows the preferred configuration of cutting ridges 122 found on abrading surface 121 and their relationship to passage 126 and handle 123. Also shown is recessed area 128 in plateau planer 120 which is included to avoid damage to anatomical members such as ligaments found located in the area of the intercondylar fossa of the femur.

The above described reamer, guide, instruments and components thereof are all preferably manufactured from a suitable surgical grade of stainless steel of the type commonly employed by those skilled in the art to construct surgical tools for use in contact with the body. The exact composition of the metal from which the instruments and components thereof are constructed forms no part of the present invention and other metals suitable for use within the body and for the intended uses of the instruments may be used without altering the nature of the invention.

It should also be noted that another advantage of the present invention is that the above-described reamer, alignment guide and distal femoral surface modifying instruments can be used in modifying the surface of either the right or the left distal femoral surface.

The manner in which the method of the present invention may be carried out will now be described. The pre-operative procedures for radiographically determining the central long axis of the femur and the angle at which resection of the distal femoral surface is to be made with respect to that axis using this method is the same as is typically employed in other methods known to those skilled in the art. Thus, a single long anterior-posterior radiograph containing the shaft of the tibia and femur is made. A portion of the femoral head should also appear in this radiograph. If long radiographic film cassettes are not available, separate radiographs of the femur and tibia will give satisfactory information.

The central long axis of the femoral shaft is identified in the radiograph and the entry point for the intramedullary reamer is identified. In most cases for the normal straight femur, this entry point lies just medial to the deepest portion of the intercondylar groove. FIG. 14 depicts the distal femoral surface 140 of the right femur showing medial condyle 141, the lateral condyle 142, the intercondylar groove 143, the posterior condylar surface 144, the anterior condylar surface 145 and the patellar surface 146. Circle 148 marks a typical entry point for the intramedullary reamer which is later followed by the femoral alignment guide. Choosing a position lateral to circle 148 will result in slightly more valgus after a femoral prosthesis is implanted while choice of a position medial to circle 148 results in decreased valgus positioning.

For most straight femurs, a point in the center of the bone at the isthmus midway between the outer cortical surfaces is chosen. A similar point 3½"–4" (89–102 mm) distally is determined (from the radiographs). A line between these two points marks the central long axis of the femur. This axis almost always crosses the distal surfaces 140 of the femur just medial to the deepest point in the anterior intercondylar groove 143, and this is where the entry point 148 is placed for the reamer and intramedullary alignment guide.

In patients with a varus bow of the femur, the central long axis of the middle one-third of the femur should be determined from the radiographs and the entry point should be marked at the point in the intercondylar groove that is intersected by this axis. This will place the point of entry somewhat more lateral than usual in the intercondylar groove 143. If alignment is made with respect to a more proximal portion of the femur, the entry point will be placed even farther laterally and will align the knee in excessive valgus, placing the central point of the knee medial to the hip.

In many patients, the distal femur has a valgus curve. If this is not taken into consideration and accommodated when choosing the entry point and placing reamer and alignment guide in the femur, the knee will align in excessive valgus. In order to prevent misalignment, the central long axis is taken from the isthmus and the distal one-third of the femur. This places the entry point more medially than usual on the distal femoral surface 140.

If the femur exhibits a slight valgus curve in the distal one third of the bone, use of the entry point for a normal straight femur will result in excessive valgus. Therefore, an entry point which is slightly more medially placed than that used for a normal straight femur is appropriate. The estimated central long axis used to mark the entry point must be chosen with care. The proximal center point of the axis should be in the isthmus and the distal point should be in the proximal portion of the distal one third of the bone (3½–4" distal to the point in the isthmus).

The radiographs are also employed in a known manner to determine the angle shown by reference numeral 8 of FIG. 4 to be used in selecting intramedullary alignment guide 30 for a particular patient. Generally, intramedullary alignment guides having angles shown by reference numeral 8 of 3°, 5°, 7° and 9° are typically used with 5° being most commonly used.

Operatively, the usual surgical approach is made. After the anterior aspect of the knee is exposed, the knee is flexed to 100° so that the posterior curved surfaces of both femoral condyles can be visualized. Partial excision of the fatpad may be necessary.

The intercondylar notch 143 is cleared of osteophytes. A "Duckbill" rongeur is used to expose the posterior cruciate ligament attachment to the medial femoral condyle. The previously determined entry point on the distal femoral surface is flattened and prepared with a duckbill rongeur. This is usually a point just anterior to the lateral fibers of the posterior cruciate ligament. The preceding operative approach is not illustrated and for the purposes of clarity, soft tissue, ligaments and other nonessential elements have been eliminated from FIGS. 14–23 for the purposes of clarity.

When the preferred embodiment of intramedullary reamer 10 wherein portion 13 has an outer diameter of 0.359" (9.12 mm) is used, a 3/8" (9.5 mm) outer diameter drill bit is used to bore entry point 148 through the spongy portion 154 of the femur shown in FIG. 15. FIG. 15 shows, in cross-section, a normal straight femur 150 of the right leg having a tubular shaft of hard compact (cortical) bone surrounding intramedullary canal 156 and having areas of spongy bone 154 at both ends of the shaft. Reference numeral 140 shows the distal femoral surface. After the drill bit is removed, portion 13 of intramedullary reamer 10 is inserted into the bored entry point and handle 18 is employed to impart a twisting motion to reamer 10 as portion 13 is advanced through the intramedullary canal 156. As the compact bone surfaces narrow, portion 13 is caused to follow the canal 156 and when portion 13 is completely inserted into canal 156 as shown in FIG. 15, the central long axis of the femur is now found to lie along the central long axis of reamer 10. The advantage of using the reamer 10 to find the central long axis of femur 150 is that the reamer follows the intramedullary canal if a reasonable amount of force is used to advance the reamer and a slight deformity in the femur which would tend to cause an alignment guide to deviate from the correct axis is overcome because the cutting ridges cut sideways through the deformity and the main portion of portion 13 is guided by the long inner surface of canal 156. Excessive amounts of force should be avoided in advancing the reamer because that can cause the reamer to cut through the hard compact bone, device from canal 156 and possibly pierce the shaft of the femur. Portion 13 should be long enough to contact a sufficient portion of the narrowest part of the intramedullary canal to bring portion 13 into alignment with the central long axis of the femur. Use of reamer 10 also has the advantage that if the center of entry point 143 should deviate slightly from the central long axis of the femur, the sideways cutting action of the cutting ridges against the distal femoral surface as it is advanced through canal 156 and brought into alignment with the central long axis of the femur causes the entry point boring to enlarge until it corresponds to that axis. Although, it may often be easier to use a shorter intramedullary reamer and intramedullary alignment guide (e.g., the lens preferred ones wherein the portion 13 is 7" (178 mm) in length), proper alignment may be sacrificed and such a reamer and guide should only be used in cases where a deformity of the femur requires the use of a shorter reamer and guide. Preferably, the previously described 10" (254 mm) intramedullary alignment guide are used whenever possible to insure that the distal femoral surface is shaped according to the proper alignment with respect to the central long axis of the femur.

The intramedullary reamer 10 is removed and anterior-posterior cutting guide 60 and intramedullary alignment guide impactor are attached to the intramedullary alignment guide 30 by means of locking bolt 68 and locking pin 44, respectively, prior to its insertion. Care must be taken to insure that flattened surface 37 is superior on the alignment guide for left knees and that flattened surface 39 is superior on the alignment guide for right knees. The latter is the case for the right femur of FIGS. 16–18. Portion 32 of guide 30 is inserted into the femur through the hole in the distal femoral surface left by reamer 10 until the locking fins 34 are just contacting bone. The rotational alignment of the intramedullary alignment guide is adjusted by using the posterior aspect of cutting guide 60 as a rotational alignment guide as depicted in FIGS. 17 and 18. The posterior aspect of the femoral condyles 144 are visualized, and guide 30 is turned so that equal amounts of the posterior aspects of the femoral condyles 142 and 144 are visible behind the lower edge of cutting guide 60 as shown in FIG. 17. FIG. 17 shows the manner in which cutting guide 60 is secured to handle 36 by means of having the lower locking bolt 68 rest on flattened surface 39 (for the right femur) while opposite flattened surface 37 faces downward. FIG. 18 shows the positioning of the cutting guide 60 and alignment guide 30 prior to being driven into place in the distal surface 140 of right femur 180. This procedure illustrates another advantage of the present invention: the distal femoral surface is easily and accurately shaped such that the prosthesis which is later affixed possesses the proper degree of rotational alignment with respect to the femur.

After the intramedullary alignment guide 30 is properly positioned, it is driven into place by striking impactor 40 with a mallet (it is preferable to use impactor 40 to avoid deforming handle 36 when guide 30 is inserted) such that stabilizing fins 34 are completely imbedded within the distal surface of the intercondylar notch as shown in FIG. 16. FIG. 16 show alignment guide 30 fully inserted within femur 150 such that portion 32 is inserted into the space in intramedullary canal 156 left by portion 13 of reamer 10 and bounded by the hard compact (cortical) bone 152 which results in the central long axis of femur 150 corresponding to the central long axis of portion 132. Guide handle 36 is bent away from the central long axis of the femur such that the central long axis of handle 36 deviates from that axis of the femur by a preselected angle thereby enabling the distal femoral surface modifying instruments to shape the distal femoral surface in the desired relationship to that femoral axis.

Impactor 40 and cutting guide 60 are then removed and distal femoral condyle cutting guide 80 having main body 81 and cutting guideplate 82 is placed on guide handle 36 and moved forward until the cutting guide surface 83 (not shown) is positioned to remove the desired amount of bone (approximately the thickness of the distal portion of the femoral prosthesis component). Cutting guide 80 is secured to handle 36 by means of locking bolt 88. A saw blade 190 having saw teeth 192 is placed against cutting guide surface 83 (not shown) on the femoral side of guideplate 82 and a rough cut of each of the two distal femoral condyles is made, one cut on each femoral side of guideplate 82.

Cutting guide 80 is removed and the rough cut is completed if the surgeon was not able to completely cut through the condyles with cutting guide 80 attached. As shown in FIG. 20, plateau planer 120 is used to flatten the rough cut distal femoral surface by twisting handle 123 back and forth to adjust that surface to the chosen degree of valgus as a result of the fact that planer 120 cooperatively fits over handle 36 and the planar surface 121 of planer 120 is automatically oriented at the chosen angle of valgus as a result of the relationship of guide handle 36 to portion 32 of guide 30. Planar surface 121 is preferably large enough so that the lateral aspects of the femoral condyles are not left with a ridge. If a small ridge remains after the distal femoral surface is flattened to the proper shape with planer 120, the remaining ridge is trimmed away using an oscillating saw. The plateau planer produces a much smoother and planar surface than is usually the case with an oscillating saw because such saws tend to ride over hard bone and cut into the softer areas on the femoral surface. The plateau planer cannot ride over the hard bone and results in a very level surface because the handle 36 holds its planar abrading surface 121 in place. The resulting planar surface provides a firm mounting for a prosthesis and enables the maximum amount of distal femoral surface to contact the surface of a distal femoral prosthesis.

Plateau planer 120 is then removed from guide handle 36 and anterior-posterior cutting guide 60 is reinserted onto handle 36 and placed against the flattened portion of the distal femoral surface of femur 150 and secured to handle 36 by means of locking bolt 68 as shown in FIG. 21. The superior surface 212 of cutting guide 60 is used as a saw guide in resecting the medial and lateral anterior femoral condyles. The superior surface of slot 66 shown with blade 210 resting against that surface and the superior surface of slot 64 (not shown) are used to guide the resection of the posterior medial and lateral condyles. In making the resections, care should be taken to keep the saw blade flat against the surface of the cutting guide 60 being used to guide the saw blade.

Cutting guide 60 is removed from handle 36 and, as shown in FIG. 22, bevel cutting guide 100 is placed on guide handle 36 and secured thereto by means of locking bolt 106 in main body 107. The back surface 109 of cutting guide 100 should fit flatly and firmly against the distal surface of femur 150 before the resections are made. Bone and cartilage debris may need to be removed from around the base of guide handle 36 to allow proper seating of cutting guide 60. The medial condyles are resected by bringing a saw blade across guideplates 101 and 102 to obtain resected anterior condylar surface 220 and resected posterior condylar surface 221 after resection is completed. The same process (not shown) is repeated for the lateral condyles using guideplates 103 and 104. Care must be taken to insure that the saw blade employed to resect the condyles lies flat against the surface of the guideplates 101, 102, 103 and 104. As noted earlier for other instruments, it may be necessary to remove cutting guide 100 to complete the resection of the condyles. FIG. 22 also shows the results of the resections performed in the previous step using cutting guide 60 as bevelled anterior surface 220 and bevelled posterior surface 221.

The cutting guide 100 and intramedullary alignment guide 30 is removed and the small bridge of bone remaining between the two anterior bevelled distal medial and lateral surfaces of femur 150 is trimmed flat using an oscillating saw.

The resulting shaped distal femoral surface of femur 150 is depicted in FIG. 23 showing the medial side of femur 150 with resected anterior surfaces 220 and 223 and resected posterior surfaces 221 and 222 situated about the flat distal femoral surface 224. That shaped surface is fitted with a preselected distal femoral prosthesis of the type which is well known in the art having an interior surface selected to properly fit over the shaped distal femoral surface in accordance with fitting techniques which are well known to those skilled in the art and which form no part of the present invention. It is of course understood that the dimensions and the angles at which the guideplates are set on the distal femoral surface modifying instruments will vary depending upon the specific type of prosthesis selected. It is well within the power of those skilled in the art to design suitably dimensioned and angled instruments for a particular prosthesis. One type of a prosthesis is shown in outine form as reference numeral 230 having peg 231 which extends into femur 150 to secure the prosthesis onto the distal portion of the femur. After the prosthesis has been inserted, the wound may then be closed in the usual manner employed for such prostheses. In the alternative, the tibia may be prepared to receive a tibial knee prosthesis of the type commonly employed when a total knee implant is to be inserted prior to insertion of the distal femoral prosthesis and thereafter both a tibial and a distal femoral prosthesis may be inserted in a manner well known to those skilled in the art.

Other modifications and variations of the method and apparatus of the present invention will become apparent to those skilled in the art from an examination of the above specification and drawings. Therefore, other variations of the present invention may be made which fall within the scope of the appended claims even though such variations were not specifically discussed above.

That which is claimed is:

1. A method of preparing a human femur having a distal femoral surface containing medial and lateral condyles and an intramedullary canal located at the center of a tubular shaft of hard compact bone to receive a distal femoral knee prosthesis, said method comprising the steps of
   (A) boring an entry point for an intramedullary reamer through the distal femoral surface between the medial and laterial condyles at a point approximating the central long axis of the femur,
   (B) advancing an intramedullary reamer through said entry point along the intramedullary canal for a sufficient distance to enable the central long axis of said reamer to correspond with the central long axis of the femur, said reamer comprising a rod having a portion which is intended to enter the intramedullary canal which portion (1) is of a diameter approximating the narrowest portion of said intramedullary canal and (2) has a plurality of cutting ridges situated about its circumference, the remaining portion of said rod having a means for imparting a twisting motion to said reamer,
   (C) replacing said reamer with an intramedullary alignment guide fixed in a suitable aligning relationship with respect to the distal femoral surface, said intramedullary alignment guide comprising (1) an intramedullary rod portion adapted to fit in a space left in the femur upon removal of said reamer, (2) a guide handle attached to and set at a preselected angle with respect to the central long axis of said intramedullary rod portion and being adapted to receive at least at least one femoral surface modifying instrument in proper alignment with respect to said handle and (3) a means for securing the combination of (1) and (2) in a fixed position in the femur, wherein the central long axis of said rod portion corresponds to the central long axis of said femur,
   (D) attaching at least one distal femoral surface modifying instrument to said guide handle, said instrument being adapted to cooperatively engage said handle and to assume an appropriate fixed relationship with respect to the distal femoral surface and to the central long axis of the femur as a result of its alignment with respect to the handle, said instrument being further designed to aid in shaping the distal femoral surface in such a manner that a preselected distal femoral knee prosthesis can be attached to said surface,
   (E) modifying the surface through the use of said instrument,
   (F) repeating steps (D) and (E) as needed until an appropriately shaped distal femoral surface is obtained,
   (G) removing the intramedullary alignment rod and
   (H) trimming any remaining bone from the distal femoral surface.

2. The method as claimed in claim 1 wherein at least one of the instruments employed in steps (D) and (E) is an anterior-posterior cutting guide comprising a plate having a passage passing through said cutting guide and designed to cooperatively engage said guide handle and a means for fixing said cutting guide in proper alignment with respect to said handle, said cutting guide further having an upper resection guide surface for a resecting means used to resect the anterior aspect of the femoral condyles and at least one lower resection guide surface for a resecting means used to resect the posterior aspect of the femoral condyles relative to the alignment of the handle.

3. The method as claimed in claim 1 wherein at least one of the instruments employed in steps (D) and (E) is a distal femoral condyle cutting guide comprising a main body having a passage adapted to cooperatively engage said guide handle and a means for fixing said cutting guide in proper alignment with respect to said handle, said main body containing a guideplate which is held by means of a connecting arm between the main body and the guideplate at an angle which is transverse to the central long axis of said guide handle and set at the same preselected angle with respect to the central long axis of the intramedullary rod and of the femur as is the guide handle, said guideplate having a resection means guide surface thereon for resecting the distal portion of the medial and lateral condyles of said femur.

4. The method as claimed in claim 1 wherein at least one of the instruments employed in steps (D) and (E) is a plateau planer comprising a planar abrading surface, a handle and a shaft connecting said planar abrading surface to said handle, said planer having a passage therethrough adapted to cooperatively engage said guide handle and to allow the planar abrading surface to be transversely rotated about the central axis of said guide handle while it is in contact with the distal femoral surface to flatten said distal femoral surface transversely with respect to the central long axis of the guide handle, said planar abrading surface containing a plurality of spaced cutting ridges which are planar and are situated transverse to the central long axis of said guide handle and further having a recessed area thereon to avoid damage to anatomical members found below the intercondylar fossa of the femur.

5. The method as claimed in claim 1 wherein at least one of the instruments employed in steps (D) and (E) is a bevel cutting guide comprising a main body having a passage therethrough adapted to cooperatively engage said guide handle and a means for fixing said cutting guide in proper alignment with respect to said handle, there being a plurality of bevel cutting guideplates attached to said main body and situated at an appropriate angle with respect to a flattened distal femoral surface such that the anterior and posterior aspects of the femoral condyles can be resected to produce a suitably bevelled distal femoral surface.

6. As an article of manufacture, a distal femoral surface shaping guide comprising the combination of
(A) an intramedullary alignment guide comprising (1) an intramedullary rod portion adapted to closely fit in and extend through the narrowest portion of a human femur such that the central long axis of said femur passes through the central long axis of said intramedullary rod portion, (2) a guide handle attached to and set at a preselected angle with respect to said axis of the intramedullary rod portion and being adapted to receive at least one femoral surface modifying instrument in proper alignment with respect to said handle and (3) a means for securing the combination of (1) and (2) in a fixed position in the femur with
(B) a least one femoral surface modifying instrument which is adapted to cooperatively engage said handle and to assume an appropriate fixed relationship with respect to the distal femoral surface and to the central long axis of the femur, said instrument being further designed to aid in shaping the distal femoral surface in such a manner that a preselected femoral knee prosthesis can be attached to said surface.

7. The article as claimed in claim 6 wherein at least one of the instruments employed in said (B) is an anterior-posterior cutting guide comprising a plate having a passage passing through said cutting guide and designed to cooperatively engage said guide handle and a means for fixing said cutting guide in proper alignment with respect to said handle, said cutting guide further having an upper resection guide surface for a resecting means used to resect the anterior aspect of the femoral condyles and at least one lower resection guide surface for a resecting means used to resect the posterior aspect of the femoral condyles relative tothe alignment of the handle.

8. The article as claimed in claim 6 wherein at least one of the instruments employed in said (B) is a distal femoral condyle cutting guide comprising a main body having a passage adapted to cooperatively engage said guide handle and a means for fixing said cutting guide in proper alignment with respect to said handle, said main body containing a guideplate which is held by means of a connecting arm between the main body and the guideplate at an angle which is transverse to the central long axis of said guide handle and set at the same preselected angle with respect to the central long axis of the intramedullary rod and of the femur as is the guide handle, said guideplate having a resection means guide surface thereon for resection the distal portion of the medial and lateral condyles of said femur.

9. The article as claimed in claim 6 wherein at least one of the instruments employed in said (B) is a plateau planer comprising a planar abrading surface, a handle and a shaft connecting said planar abrading surface to said handle, said planer having a passage therethrough adapted to cooperatively engage said guide handle and to allow the planar abrading surface to be transversely rotated about the central axis of said guide handle while it is in contact with the distal femoral surface to flatten said distal femoral surface transversely with respect to the central long axis of the guide handle, said planar abrading surface containing a plurality of spaced cutting ridges which are planar and are situated transverse to the central long axis of said guide handle and further having a recessed area thereon to avoid damage to anatomical members found below the intercondylar fossa of the femur.

10. The article as claimed in claim 6 wherein at least one of the instruments employed in said (B) is a bevel cutting guide comprising a main body having a passage therethrough adapted to cooperatively engage said guide handle and a means for fixing said cutting guide in proper alignment with respect to said handle, there being a plurality of bevel cutting guideplates attached to said main body and situated at an appropriate angle with respect to a flattened distal femoral surface such that the anterior and posterior aspects of the femoral condyles can be resected to produce a suitably bevelled distal femoral surface.

* * * * *

UNITED STATES PATENT AND TRADEMARK OFFICE
CERTIFICATE OF CORRECTION

PATENT NO. : 4,474,177
DATED      : October 2, 1984
INVENTOR(S) : Leo A. Whiteside It is certified that error appears in the above-identified patent and that said Letters Patent is hereby corrected as shown below:

In column 3, line 27, "long" should read -- along --.

In column 4, line 28, "it)" should read -- it --.

In column 8, line 42, "device" should read -- deviate --.

In column 8, line 56, "lens" should read -- less --.

In column 8, line 62, "are" should read -- is --.

In column 9, line 42, "132" should read -- 32 --.

In column 11, line 42, "laterial" should read -- lateral --.

In column 11, line 65, "at least at least one" should read -- at least one --.

Signed and Sealed this

Twenty-third Day of September 1986

[SEAL]

Attest:

DONALD J. QUIGG

Attesting Officer

Commissioner of Patents and Trademarks